United States Patent [19]

Kohno et al.

[11] Patent Number: 4,795,911
[45] Date of Patent: Jan. 3, 1989

[54] SURFACE EXAMINING APPARATUS FOR DETECTING THE PRESENCE OF FOREIGN PARTICLES ON THE SURFACE

[75] Inventors: Michio Kohno, Tokyo; Eiichi Murakami, Yokohama; Akiyoshi Suzuki, Tokyo, all of Japan

[73] Assignee: Canon Kabushiki Kaisha, Tokyo, Japan

[21] Appl. No.: 14,033

[22] Filed: Feb. 12, 1987

[30] Foreign Application Priority Data

Feb. 14, 1986 [JP] Japan ................................. 61-30360
Feb. 14, 1986 [JP] Japan ....................................... 30361
Feb. 14, 1986 [JP] Japan ....................................... 30363

[51] Int. Cl.$^4$ ............................................. G01N 21/88
[52] U.S. Cl. ................................... 250/572; 356/237
[58] Field of Search ...................... 250/572, 562, 563; 356/237, 239, 338, 430, 431

[56] References Cited

U.S. PATENT DOCUMENTS 4,610,541 9/1986 Tanimoto et al. ................... 250/572
4,669,875 6/1987 Shiba et al. .......................... 250/572

Primary Examiner—Edward P. Westin
Attorney, Agent, or Firm—Fitzpatrick, Cella, Harper & Scinto

[57] ABSTRACT

An apparatus usable with an object having a surface with a pattern, for examining the state of the surface, includes a projecting system for directing a light beam to the surface of the object, and a collecting system for collecting scattered light from the surface of the object. A projection of the optical axis of the collecting system onto the surface of the object extends in a direction different from a projection onto the surface of the object of a major portion of light diffracted from the pattern. A light-receiving unit receives the scattered light as collected by the collecting system and for producing an output corresponding to the state of the surface of the object.

2 Claims, 7 Drawing Sheets

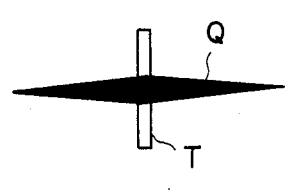
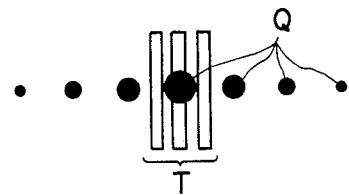
FIG. 5A      FIG. 5B
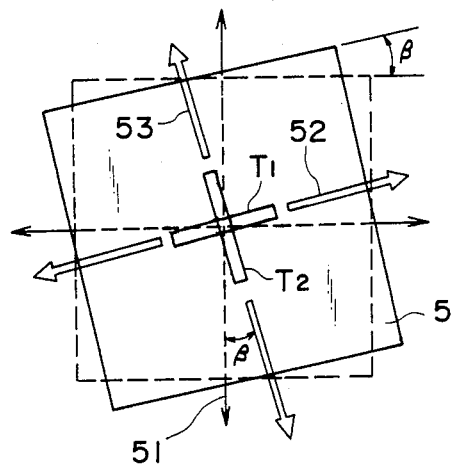
FIG. 5C

SURFACE EXAMINING APPARATUS FOR DETECTING THE PRESENCE OF FOREIGN PARTICLES ON THE SURFACE

FIELD OF THE INVENTION AND RELATED ART

This invention relates to a surface examining apparatus for detecting the state of a surface of an object and, more particularly, to a surface examining apparatus for detecting, with high-accuracy, the present or absence of any dust or foreign particles adhered to a surface of an object. The examining apparatus of the present invention is particularly suitably usable in the field of manufacture of semiconductor devices such as integrated circuits, for detecting dust or foreign particles which are adhered to a plate-like member such as a reticle or photomask having a circuit pattern formed thereon, or which are adhered to a pellicle protecting film provided over the reticle or photomask.

The manufacture of semiconductor devices such as integrated circuits involves a photolithographic process wherein an exposure apparatus such as a stepper or a mask aligner is used to photolithographically transfer, onto a semiconductive or silicon wafer, a circuit pattern formed on a glass plate such as a reticle or photomask. If, in such photoprinting process, a photomask on which foreign particles are deposited is used, images of these foreign particles as well as an image of the circuit pattern of the photomask are photoprinted on the wafer, with the result that the yield of semiconductor devices is disadvantageously decreased. It is accordingly desired to examine the reticle or photomask, in the course of manufacture of semiconductor devices, so as to detect the presence or absence of any dust or foreign particles on such glass plate. There have been proposed various types of examining apparatuses and methods. Examples are disclosed in Japanese Liid-Open Patent Application, Laid-Open No. 162038/1981 filed by the assignee of the subject application, U.S. Pat. Nos. 4,468,120 and 4,541,475, Japanese Laid-Open Patent Applications, Laid-Open Nos. 12341/1984, 12342/1984 and 82727/1984.

FIG. 1 schematically shows a basic structure of a surface examining apparatus of the type such as disclosed in the aforementioned U.S. Pat. No. 4,468,120 and as is known. In this type of examining apparatus, detection of any foreign particle is accomplished by utilizing the phenomenon that, when a light is incident on the foreign particle, it scatters the light, particularly isotropically or non-directionally.

In the structure illustrated in FIG. 1, a light beam from a laser 10 is directed by way of a scanning mirror 11 and a lens 12 to a mirror 13 by which the light beam is projected upon a surface of a glass plate 15 by way of a mirror 14. Further, by rotationally or vibrationally moving the scanning mirror 11, the surface of the plate 15 is scanned along a line. Also, by moving the glass plate 18 in the direction of an arrow S1 or S2, the whole surface of the plate 18 is scanned with the light beam from the scanning mirror 11. For the examination of the surface of the glass plate 18, a plurality of light-receiving elements 16, 17 and 18 are provided at positions that are spaced from the path of a light directly reflected from the glass plate 18 and from the path of a light transmitted through the glass plate 18. By use of output signals from these light-receiving elements 16-18, any foreign particle deposited on the surface of the plate-like member 15 is detected.

More specifically, as is well known in the art, the light incident upon a circuit pattern of a photomask or reticle is diffractively reflected by the circuit pattern, and the light rays caused by such diffraction advance with specific, direction. Therefore, when the light is diffractively or scatteringly reflected by the circuit pattern, the light-receiving elements 16-18 produce output signals of signfficantly different levels in accordance with the direction of the diffraction lights. When, on the other hand, the light is incident upon a particle deposited upon the reticle or photomask, the light is scattered isotropically or non-directionally. Accordingly, at this time, the light-receiving elements 16-18 produce output sinnals of substantially the same level. Thus, by comparing the outputs of the light-receiving elements 16-18, the presence or absence of any foreign particle on the plate-like member 15 is detected.

In the arrangement of FIG. 1, the mirror 13 is disposed retractably from the path of the light beam from the scanning mirror 11. That is, for the examination of the lower surface of the plate 15, the mirror 13 is moved out of the optical path so that the light beam from the scanning mirror 11 is projected upon the lower surface of the plate 15 by way of mirror 45, thereby to scan the lower surface.

FIG. 2 shows another example of surface examination, disclosed in the aforementioned Japanese Laid-Open Patent Application, Laid-Open No. 82727/1984. In this example, the examination is made by utilizing the phenomenon that the polarization characteristic of a scanning light beam is affected by a particle on the surface being examined. As shown in FIG. 2, a light beam from a laser 10 is incident on a polarizer 19 whereby a light beam of a predetermined state of polarization is produced. The light beam from the polarizer 19 is directed by way of a scanning mirror 11 and a lens 12 to a mirror 13, by which it is projected upon the surface of a glass plate 15 by way of a mirror 14. As in the foregoing example, the plate 15 is scanned with the light beam 1 under the influence of the scanning mirror 11. Also, two light-receiving elements 21 and 23 having analyzers 20 and 22, respectively, disposed in front of them, are provided at positions that are spaced from the path of a light directly reflected from the glass plate 15 and from the path of a light transmitted through the glass plate 15. By means of the two light-receiving elements 21 and 23, any difference in the quantity of light reception, resulting from the difference in the ratio of polarization between the diffractively reflected light from the circuit pattern and the scatteringly reflected light from the foreign particle, is detected. On the basis of this detection, the circuit pattern and the foreign particle on the glass plate 15 are discriminated. In the arrangement of FIG. 2, as in the FIG. 1 structure, the mirror 13 is made retractable from the path of the light from the scanning mirror 11.

According to the examining systems shown in FIGS. 1 and 2, the directly reflected component and the transmitted component of the scanning laser beam 1 do not enter into the light-receiving elements. However, a portion of diffractively reflected rays from the circuit pattern, having different diffraction orders, enters into the light-receiving elements with a high possibility. Further, depending on the shape or reflection factor of the particle, the quantity of scatteringly reflected light to be received by the light-receiving elements changes.

Accordingly, where the discrimination of the circuit pattern and the particle is to be made on the basis of the difference in output level of the signals from the light-receiving elements produced in response to reception of the diffractively reflected light from the circuit pattern and the scatteringly reflected light from the particle, such difference itself is not constant for the reason described above, thus resulting in a decreased rate of detection of foreign particles.

The above-described inconveniences are not exclusively involved in the surface examining systems disclosed in the aforementioned U.S. Pat. No. 4,468,120 and Japanese Laid-Open Patent Application, Laid-Open No. 82727/1984. Similar problems have been found in the examining systems disclosed in the aforementioned Japanese Laid-Open Patent Applications, Laid-Open Nos. 162038/1981, 12341/1984 and 12342/1984.

U.S. Pat. No. 4,541,475, mentioned above, shows an examining apparatus wherein an optical axis of an optical system, constituting a light-receiving unit, is inclined with a predetermined angle relative to a surface to be examined. Such arrangement is employed in order to avoid the problem related to the diffraction of light at the circuit pattern. According to the disclosed arrangement, however, a substantial portion of the diffractively reflected light enters into the light-receiving unit, with the result that the above-described deterioration of the particle detecting rate may occur.

SUMMARY OF THE INVENTION

It is accordingly a primary object of the present invention to provide a surface examining apparatus by which any foreign particle on a plate-like member such as a reticle or photomask, can be exactly detected, while being discriminated from a circuit pattern.

It is another object of the present invention to provide a surface examining apparatus by which any foreign particle on a surface, being examined, can be exactly detected with a high detection rate.

In accordance with one preferred form of the present invention, to achieve these objects, there is provided a surface examining apparatus wherein irradiating means is provided to project a light beam upon a surface of an article on which a pattern is formed. The irradiating means is arranged to scan the surface of the article with the light beam. Light-receiving means is provided to receive light scatteringly reflected from the article and, on the basis of an output signal from the light-receiving means, the state of the surface of the article is examined. The light-receiving means includes a light-collecting portion having an optical axis. A projection of the optical axis of the light-collecting portion onto the surface of the article extends in a direction different from a projection onto the surface of the article of a major portion of light diffracted from the pattern.

In accordance with another preferred form of the present invention, there is rrovided a surface examining apparatus wherein light-projecting means is provided to project a light beam upon a surface of an article having a pattern, from above the article and in an inclined direction relative to the article, thereby to scan the article with the light beam. Light-receiving means is provided to receive light scattered by the article and, on the basis of an output signal from the light-receiving means, the state of the surface of the article is examined. A projection of the optical axis of the light-collecting portion onto the surface of the article extends in a direction different from a projection onto the surface of the article of a major portion of light diffracted from the pattern.

Particularly, in accordance with a preferred feature of the present invention, the optical axis of the light-collecting portion of the light-receiving means is on a side of a normal to the surface being examined, in which side the light beam is incident upon the surface. With this arrangement, the foreign particles on the surface can be exactly detected with an increased detection rate, while being discriminated from the pattern on the surface.

In accordance with another aspect of the present invention, the optical axis of the light-collecting portion, as projected upon the surface of the article, defines an angle with respect to a reference direction determined for the article in the range of 15±5 degrees. In other words, the optical axis of the light-collecting portion as projected upon the surface being examined, defines an angle in the range of 15±5 degrees relative to the direction of advancement, as projected on the plane of the surface being examined, of the light diffracted by the major or proper and desired pattern on the surface being examined.

In accordance with a further feature of the present invention, the optical axis of the light-collecting portion has an angle in the range of ±45 degrees relative to the optical axis of a light projecting portion of the light projecting means.

According to a still further feature of the present invention, a common optical system is used for the light-collecting portion and a portion of the light projecting means. This makes the structure simple and compact.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIGS. 5A and 5B are explanatory views, respectively showing examples of diffraction by different types of circuit patterns.

FIG. 5C is an explanatory views showing the relation between the direction of the optical axis of a light-collecting portion of a light receiving means, used in the apparatus of FIG. 3, and the direction along which the diffracted light advances.

DESCRIPTION OF THE PREFERRED EMBODIMENTS

Figure 1:
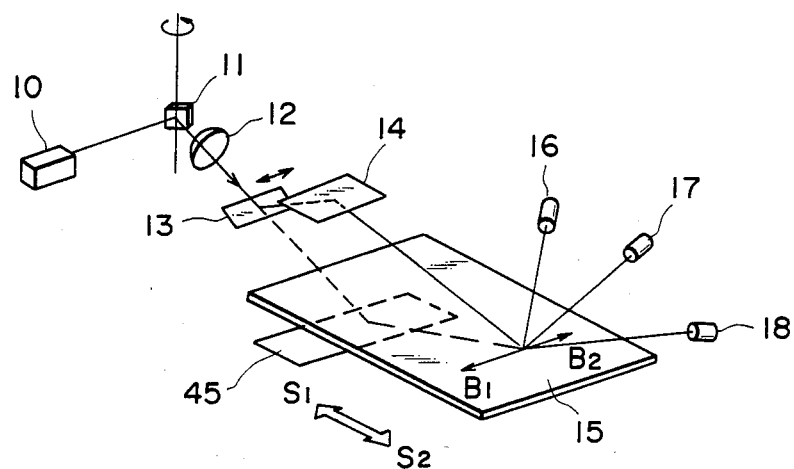
FIGS. 1 and 2 are schematic views, respectively, showing examples of known type surface examining apparatuses.
Figure 2:
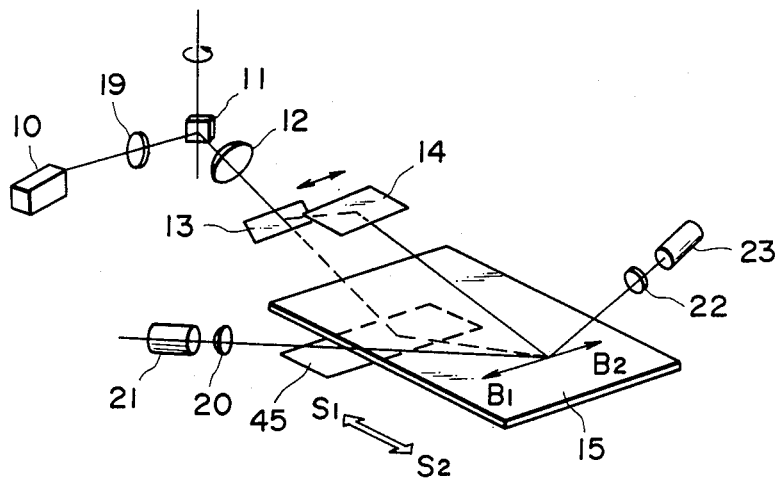
Figure 3:
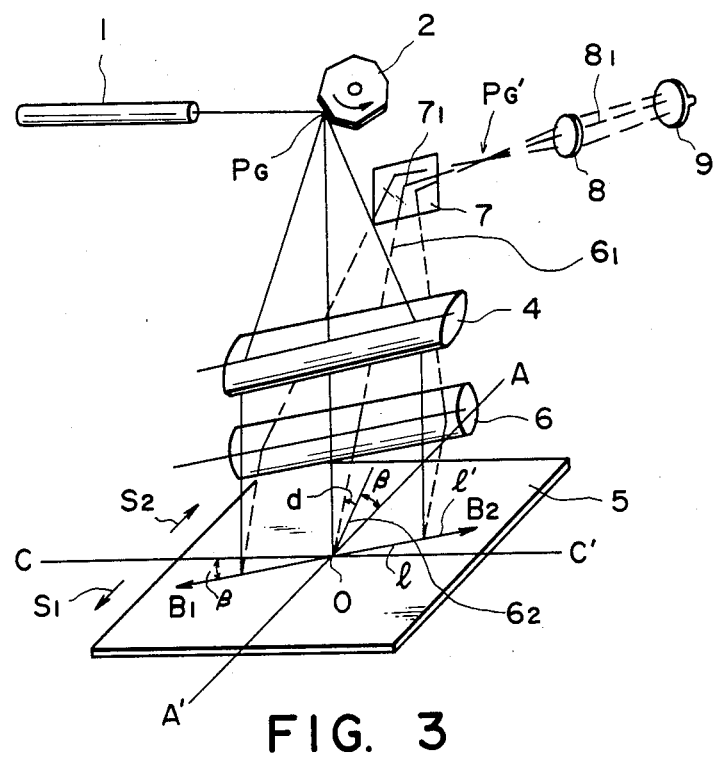
FIG. 3 is a schematic view showing an optical arrangement of a major portion of a surface examining apparatus according to a first embodiment of the present invention.

Referring now to FIG. 3, there is shown an optical arrangement of a major portion of a surface examining apparatus according to an embodiment of the present invention.

As shown, the examining apparatus includes a light source 1 such as a laser source for producing a laser beam, and a deflector 2 such as a polygonal mirror for scanningly deflecting the laser beam from the source 1. The lasrr beam deflected by the polygonal mirror 2 is incident on a light projecting optical system 4 which comprises a lens optical system including an f-$\theta$ lens and other elements. By this projecting system 4, the laser beam is perpendicularly incident upon the subject of examination, denoted at reference numeral 5, which in this example is a reticle used for the manufacture of semiconductor devices. A light-collecting optical system 6, comprising a lens optical system, is provided to collect light rays scattered (in this embodiment, scatteringly reflected) by dust or foreign particles deposited on the reticle 5. Mirror 7 is provided to reflect the scatteringly reflected light as collected by the collecting system 6, whereby the light from the collecting system 6 is directed to a lens system 8. Photodetector 9 is provided to receive the scatteringly reflected light as collected at or in the vicinity of a point $P_G'$ and passed through the lens system 8.

In the illustrated arrangement, the light beam from the laser 1 is reflected by the polygonal mirror 2 to the projecting system 4, by which it is converged, at one moment, upon a point (e.g. O) on the reticle 5 on which a circuit pattern is formed. The projecting system 4 has an optical axis which extends perpendicularly to the reticle 5 surface.

The polygonal mirror 2 and the projecting system 4 are cooperative with each other to provide a portion of light-projecting means. By rotating the polygonal mirror 2, the light beam from the laser 1 is scanningly deflected such that the surface of the reticle 5 is scanned in a direction from a point B1 to a point B2. Also, the reticle 5 is moved by suitable driving means, not shown, in a direction of an arrow S1 or S2. By this arrangement, substantially the whole surface of the reticle is scanned with the light beam from the laser 1.

In the present embodiment, the light beam which is incident upon a position $P_G$ on the polygonal mirror 2 is a parallel beam, which is converged by the action of the projecting system 4 so that a beam spot is formed on the surface of the reticle 5. To achieve this, the projecting system 4 and the reticle 5 are spaced by a distance corresponding to the focal length of the lens optical system of the projecting system 4.

Further, in the present embodiment, the light-collecting system 6 is disposed above the reticle 5 so as to collect at least a portion the scatteringly reflected light rays from any particle on the reticle 5. The collecting system 6 is adapted to collect the scatteringly reflected light at a position of the point $P_G'$ or in the vicinity thereof, and the thus collected light is directed to the light-receiving surface of the photodetector 9 by way of the lens system 8. The collecting system 6, the mirror 7 and the lens system 8 are cooperative with each other to provide a portion of light-receiving means. The lens system 8 has an optical axis denoted at $8_1$ whose extension intersects the mirror 7 at a point $7_1$. The line connecting this intersection point $7_1$ and the point O on the reticle 5 corresponds to the optical axis $6_1$ of the collecting system 6. Also, the line connecting the point O and the reflection point $P_G$ on the polygonal mirror 2 corresponds to the optical axis of the projecting system 4.

It will be understood that the point $P_G'$ denotes the position at which or in the vicinity of which the light beam, having been emitted from the reflection point $P_G$ on the rotating polygonal mirror 2 and having been incident upon the reticle 5 by way of the projecting system 4 and further having been scatteringly reflected by a particle on the reticle 5, is collected by means of the collecting system 6. Stated differently, the lens optical system of the collecting system 6 has such refractive power, in respect to the direction of a scan line determined by the projecting system 4, that the focal point position of the collecting optical system is coincident with or substantially coincident with the pssition $P_G'$.

An important feature of the present invention is as follows: a projection $6_2$ of the optical axis $6_1$ of the collecting system 6 onto the surface of the reticle 5 extends in a direction different from a projection (e.g. A–A') onto the surface of the reticle 5 of a major portion of light diffracted by the primary pattern on the reticle. That is, the optical axis $6_1$ of the collecting system 6, when projected upon the reticle 5 surface, extends in a direction which deviates from the direction of diffraction at the primary pattern on the reticle 5, by an angle $\beta$. The direction of the optical axis $6_1$ of the collecting system 6, when it is projected upon the reticle 5 surface, is depicted in FIG. 3 by a line $6_2$ that rotationally deviates from a line A—A', which is a reference direction corresponding to one of primary diffraction directions, as will be described later. Accordingly, the optical axis $6_1$ of the collecting system 6 has an azimuth "$\beta$".

In accordance with another important feature of the present invention, the scan of the reticle 5 surface with the light beam scanningly deflected by the rotating polygonal mirror 2 is made such that the line l connecting the points B1 and B2, i.e. the scan line l as determined by the one-dimensional scanning, extends in a direction different from the direction of diffraction caused by the primary pattern formed on the reticle 5. More preferably, the scan of the reticle 5 surface is made so that the scan line l rotationally deviates from the direction of diffraction at the primary pattern by an angle equal to the above-described angle $\beta$.

Where a plane which contains the optical axis $6_1$ of the collecting system 6 and the image ($6_2$) of the same, as being projected upon the reticle 5 surface, is called a "meridional plane", a plane that is perpendicular to the meridional plane and that contains the optical axis $6_1$ of the collecting system 6 is a "sagittal plane". In the present embodiment, the optical components are so arranged that the line l defined on the reticle 5 surface by the scanning beam incident thereupon and the line l' along which the sagittal plane of the collecting system 6 intersects the reticle 5 surface, are substantially coincident with each other. Such arrangement is employed in order to collect the scatteringly reflected light rays efficiently so that a larger amount of light is directed to the photodetector 9.

It is to be noted however that the exact coincidence between the scan line l and the line l' of intersection of the sagittal plane of the collecting system 6 with the reticle 5 surface, is not always required. These lines may be deviate from each other within a range in which a sufficient amount of scatteringly reflected light from a foreign particle can be collected. It is also to be noted that the scan line l determined on the reticle 5 surface by the scanning beam from the projecting system 4 may be coincident with the direction of diffraction (diffracted light) caused by the primary pattern of the reticle 5, on the condition that the collecting system 6 is disposed with its optical axis $6_1$, when projected upon the reticle 5 surface, extending in a direction different from the direction of diffraction caused by the primary pattern of the reticle 5.

Figure 4:
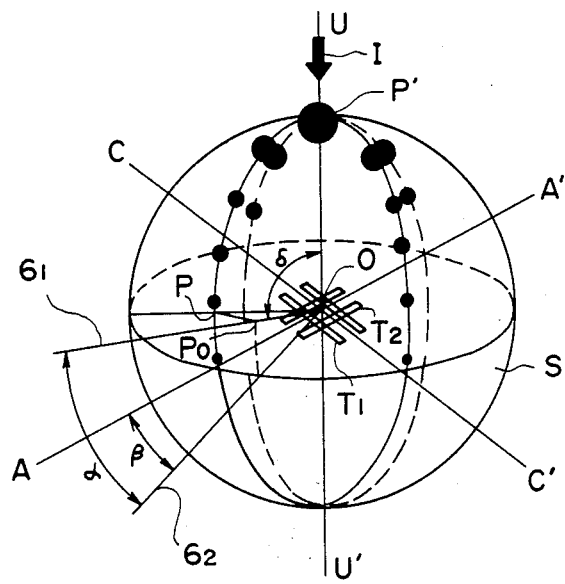
FIG. 4 is an explanatory view showing the relation between a light beam incident upon the surface being examined and the diffractively reflected light rays from a circuit pattern formed on the surface being examined.

FIG. 4 is an illustration showing a light beam projected upon the reticle surface, in the FIG. 3 embodiment, and diffractively reflected light caused by the circuit pattern of the reticle 5. In FIG. 4, the pattern bearing surface of the reticle 5 is depicted as being coincident with the equatorial plane of a sphere S which is schematically illustrated for explanation. Almost all the circuit patterns formed on photomasks or reticles, currently used in the manufacture of semiconductor devices, are provided by orthogonally extending pattern elements such as depicted at T1 and T2 in FIG. 4. When a light beam is projected upon these pattern elements T1 and T2 formed on the reticle 5 surface, perpendicularly along the direction of an arrow I, light which is directly or specularly reflected from the reticle 5 goes back along its oncoming path so that it intersects the sphere S at a point P'. Accordingly, as is well known in the art, images of diffraction lights (diffraction patterns) of different diffraction-orders are formed on the sphere S surface about the point P' and along directions each being orthogonal to a corresponding one of the pattern elements T1 and T2. If the circuit pattern is provided by a single rectilinearly extending pattern element such as depicted at T in FIG. 5A, there occurs an uninterrupted diffraction image (diffraction pattern) such as depicted at Q in FIG. 5A, that elongates in a direction orthogonal to the pattern element T. On the other hand, where the circuit pattern is provided by a combination of rectilinearly extending pattern elements, such as depicted at T in FIG. 5B, there occurs discrete diffraction images (diffraction patterns) such as depicted at Q in this Figure. In the case of FIG. 4, the circuit pattern is formed by two sets of orthogonally extending pattern elements T1 and T2. Therefore, on the surface of the sphere S, discrete diffraction images (diffraction patterns) are formed along two orthogonal directions, as seen from FIG. 4.

In any one of the cases of FIGS. 4, 5A and 5B, the intensity or magnitude of the diffraction pattern decreases with the increasing distance from the point P' on which the specularly reflected light is incident. In the case of FIG. 4, the diffractively reflected lights from the pattern elements T1 advance substantially along a plane that contains the point P' and a line A—A'. On the other hand, the diffractively reflected lights from the pattern elements T2 advance substantially along a plane that contains the point P' and a line C—C'. Therefore, in eachof the plane A—P'—A' and the plane C—P'—C', the intensity or magnitude of the diffraction pattern formed on the sphere S surface decreases rapidly with the increasing distance from the point P' in each plane. As compared therewith, when a light beam is incident on a foreign particle, the light beam is scattered by the particle, particularly isotropically or non-directionally. In view of this, according to the present embodiment, the light-collecting system of the light-receiving means is so arranged that the optical axis $6_1$ of the collecting system is disposed as far as possible from the path of the specularly reflected light and, additionally, deviated from the direction or directions of advancement of the diffracted lights caused by a primary pattern (such as at T1 and T2) of the reticle. For example, the light-collecting system 6 is disposed so that its optical axis $6_1$ extends through a point Po in FIG. 4 or passes in the vicinity thereof. That is, the optical axis $6_1$ of the collecting system 6 defines an angle "α" with respect to the surface of the reticle 5, as seen in FIGS. 3 and 4. Further, the optical axis $6_1$ of the collecting system 6, when projected upon the reticle 5 surface, deviates by an angle "β" from one of two reference directions (A—A'; or C—C') in which the diffraction lights advance, as projected upon the reticle 5 surface. With this arrangement, the effect of the diffraction lights from the circuit pattern can be minimized, with the result that substantially only the scatteringly reflected light rays from any foreign particle on the reticle 5 are received for detection by the photodetector. Output signals of the photodetector 9, representing the state of the surface of the reticle 5 are transmitted to a signal processing unit, not shown, whereby the state of the reticle 5 surface is finally determined or detected.

FIG. 5 is an illustration schematically showing the positional relation defined between the direction of the optical axis of the light-collecting system of the light-receiving means and the directions of advancement of the diffracted lights, the relation being determined in accordance with the present embodiment. In FIG. 5C, an arrow 51 denotes the direction in which the optical axis of the collecting system 6, when projected upon the reticle 5 surface, extends. Arrows 52 and 53 denote the directions in which the diffracted lights caused by the primary pattern (T1 and T2) of the reticle 5 advance. By arranging the light-collecting system 6 so as specifically to satisfy the illustrated positional relation, the undesirable effect of the diffracted lights is minimized such that substantially only the scattered lights are collected. Accordingly, any foreign particle on the reticle can be detected exactly and can be discriminated from the circuit pattern, at a higher detection rate.

While in the present embodiment, the light beam is projected upon the reticle 5 surface perpendicularly. However, this is not essential, and the light beam may be projected upon the reticle surface at an inclined angle, as will be described later with reference to several other preferred forms of the present invention.

In the FIG. 3 embodiment using perpendicular projection, it is desirable to dispose the light-collecting system so that a larger angle δ (see FIG. 4), preferably $60° < δ < 180°$, is defined by the points P' and Po with respect to the point O. This is desirable because it allows further improvement of the rate of exact discrimination of the foreign particles.

Also, in the present embodiment, it is desirable in regard to the improvement in the rate of exact discrimination of the foreign particles that the optical components are disposed so as to define an angle, not greater than ±45 degrees, between the optical axis of the collecting system 6 and the optical axis of the projecting system 4.

In some cases, the circuit pattern of a reticle or photomask includes a pattern element which is inclined by an angle of 30, 45 or 60 degrees relative to the above-described reference directions (A—A' and C—C'). The inventors of the subject application have conducted various experiments and simulations, while taking such cases into account. According to such experiments and simulations, it has been found that, in order to assure exact discrimination of any foreign particle adhered to a photomask or reticle having pattern elements extending in various directions, the light-collecting system 6 is so set that its optical axis, when projected upon the surface of the reticle, defines an angle of 15±5 degrees with respect to one of the two reference directions (A—A' and C—C') of the reticle (see FIG. 3). That is, the azimuth ($\beta$) of the optical axis of the light-collecting system is preferably in the range of 15±5 degrees.

It is to be noted that the optical axis of the light-projecting system 4 and the optical axis of the light-collecting system 6 may be on the same side of a plane that contains the line C—C' and the normal to the reticle 5 surface, or alternatively they may be on the opposite sides of such plane. In any case, the advantageous effects of the present embodiment are attainable.

In the optical arrangement shown in FIG. 3, the lens system 8 may have an optical function for forming an image of the point $P_G'$ on the light-receiving surface of the photodetector 9. Alternatively, the optical components may be arranged so as to establish an optically conjugate relation between the reticle 5 surface and the light-receiving surface of the photodetector 9 such that the light beam from the point $P_G$ (which is a parallel beam) is directed to the photodetector 9.

In accordance with the present embodiment having been described with reference to FIGS. 3-5C, a specific optical arrangement is employed so as not to receive diffracted lights from a circuit pattern of a reticle or photomask but, rather, so as to selectively receive or detect only the scattered lights (particularly, the scatteringly reflected lights) from any foreign particle on the reticle or photomask. Accordingly, the particle can be detected at a higher detection rate, while being discriminated from the circuit pattern.

Figure 6:
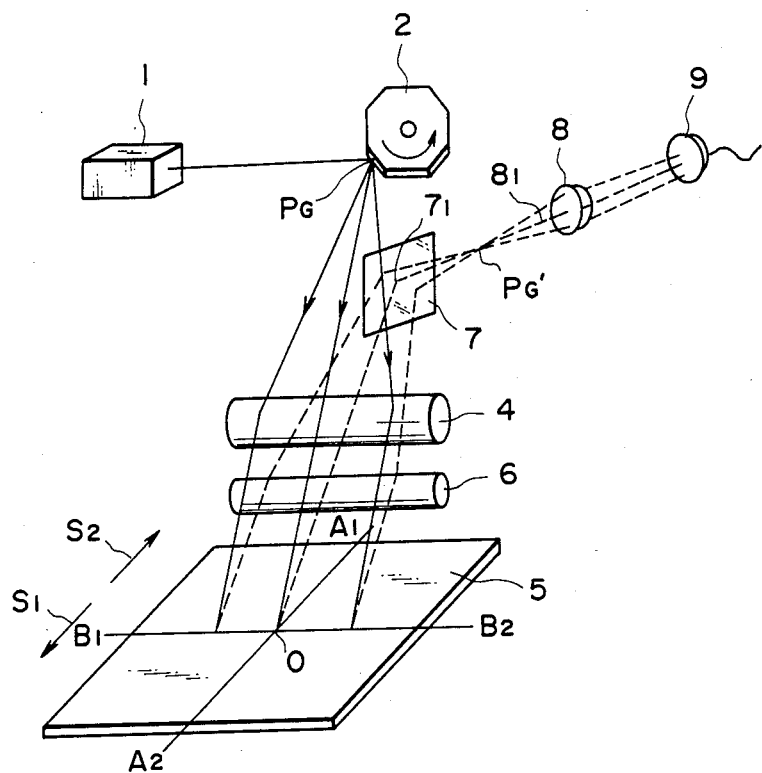
FIG. 6 is a schematic view showing an optical arrangement of a major portion of a surface examining apparatus according to another embodiment of the present invention.

FIG. 6 shows an optical arrangement of a major portion of a surface examining apparatus according to another embodiment of the present invention.

As shown, the examining apparatus includes a light source 1 such as a laser source for producing a laser beam, and a deflector 2 such as a polygonal mirror for scanningly deflecting the laser beam from the source 1. The laser beam deflected by the polygonal mirror 2 is incident on a light projecting optical system 4 which comprises a lens optical system including an f-$\theta$ lens and other elements. By this projecting system 4, the laser beam is perpendicularly incident upo the subject of examination, denoted at reference numeral 5, which in this example is a reticle used for the manufacture of semiconductor devices. A light-collecting optical system 6, comprising a lens optical system, is provided to collect light rays scattered (in this embodiment, scatteringly reflected) by dust or foreign particles deposited on the reticle 5. Mirror 7 is provided to reflect the scatteringly reflected light as collected by the collecting system 6, whereby the light from the collecting system 6 is directed to a lens system 8. Photodetector 9 is provided to receive the scatteringly reflected light as collected at or in the vicinity of a point $P_G'$ and passed through the lens system 8.

In the illustrated arrangement, the light beam from the laser 1 is reflected by the polygonal mirror 2 to the projecting system 4, by which it is converged, at one moment, upon a point (e.g. O) on the reticle 5 on which a circuit pattern is formed.

The polygonal mirror 2 and the projecting system 4 are cooperative with each other to provide a portion of light-projecting means. By rotating the polygonal mirror 2, the light beam from the laser 1 is scanningly deflected such that the surface of the reticle 5 is scanned in a direction from a point B1 to a point B2, which is perpendicular to a line $A_1$-$A_2$ in this example. Also, the reticle 5 is moved by suitable driving means, not shown, in a direction of an arrow S1 or S2. By this arrangement, substantially the whole surface of the reticle 5 is scanned with the light beam from the laser 1.

In the present embodiment, the light-projecting system 4 is diposed so that the light beam from the polygonal mirror 2 is projected upon the surface of the reticle 5 along a plane that is inclined relative to the reticle 5 surface and that intersects the reticle 5 surface along a line coincident with or in parallel to a line B1-B2 shown in FIG. 6. Also, the light-collecting system 6 is disposed so that its optical axis lies on the light entrance side of a plane that contains the line B1-B2 and a normal of the reticle 5 surface. More specifically, the light-collecting system 6 is arranged such that its optical system lies between the reticle 5 surface and the plane along which the light beam from the polygonal mirror 2 is projected upon the reticle 5 surface by the poojecting system 4. The collecting system 6 is adapted to collect a portion of the scatteringly reflected lights from any foreign particle on the reticle 5 surface, at position $P_G'$ or in the vicinity thereof, whereafter the light is directed to a light-receiving surface of the photodetector 9 by means of the lens system 8.

The collecting system 6, the mirror 7 and the lens system 8 are cooperative with each other to provide a portion of light-receiving means. The lens system 8 has an optical axis denoted at $8_1$ whose extension intersects the mirror 7 at a point $7_1$. The line connecting this intersection point $7_1$ and the point O on the reticle 5 corresponds to the optical axis $6_1$ of the collecting system 6. Also, the line connecting the point O and the reflection point $P_G$ on the polygonal mirror 2 corresponds to the optical axis of the projecting system 4.

It will be understood that the point $P_G'$ denotes the position at which or in the vicinity of which the light beam, having been emitted from the reflection point $P_G$ on the rotating polygonal mirror 2 and having been incident upon the reticle 5 by way of the projecting system 4 and further having been scatteringly reflected by a particle on the reticle 5, is collected by means of the collecting system 6.

Figure 7:
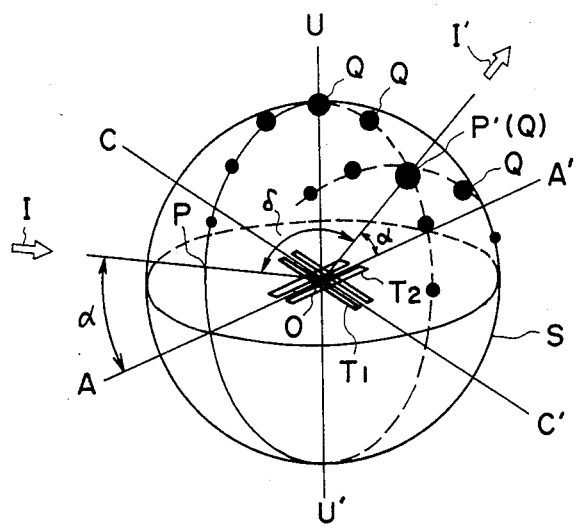
FIG. 7 is an explanatory view showing the relation between a light beam incident upon the surface being examined and the diffractively reflected light from a circuit pattern formed on the surface being examined, in a case of the FIG. 6 embodiment.

FIG. 7 is an illustration showing a light beam projected upon the reticle surface, in the FIG. 6 embodiment, and diffractively reflected light caused by the circuit pattern of the reticle 5. In FIG. 7, the pattern bearing surface of the reticle 5 is depicted as being coincident with the equatorial plane of a sphere S which is schematically illustrated for explanation. Almost all the circuit patterns formed on photomasks or reticles, currently used in the manufacture of semiconductor devices, are provided by orthogonally extending pattern elements such as depicted at T1 and T2 in FIG. 7. Where a light beam is projected upon the reticle 5 surface in a direction of an arrow I, i.e. projected at an incline from above with an incidence angle α, the plane containing a line A—A' and passing through a point u is the plane of incidence along which the beam is projected. Therefore, the light specularly reflected by the reticle 5 surface advances in the direction of an arrow I' and intersects the sphere S surface at a point P'. As has been described with reference to FIGS. 5A and 5B, there occurs an uninterrupted diffraction image (diffraction pattern) or, alternatively, discrete diffraction images (diffraction patterns) formed by diffraction lights of different diffraction orders and extending orthogonally to the pattern of the reticle. In the particular case of FIG. 7, wherein the circuit pattern comprises orthogonally extending pattern elements T1 and T2, there occur diffraction images (diffraction patterns) which are distributed substantially in two planes (A—P'—A'; C—P'—C'), as will be readily understood from the description having been made with reference to FIG. 4.

In any case, the intensity or magnitude of the diffraction image (diffraction pattern) decreases with the increasing distance from the point P' at which the specularly reflected light from the reticle 5 surface intersects the sphere S surface. Particularly, in the plane denoted by A—P'—A', the intensity of the diffraction pattern is not so high at a point of intersection at which the normal "u-O" intersects the sphere S surface, and it is very low at a point P at which the incident light beam I intersects the sphere S surface.

As for the scattered light rays from a foreign particle, on the other hand, they advance isotropically or nondirectionally as deccribed hereinbefore. Accordingly, even at the point P or in the vicinity thereof, a significantly larger amount of light from the particle will be incident on the sphere S surface.

In the present embodiment, in view of this, the light-receiving means is so arranged that the optical axis of the light-collecting system 6 is disposed as far as possible from the path of the specularly reflected light I'. More particularly, the light collecting system 6 is disposed such that its optical axis lies on the light entrance side (A-O-u) of the normal (u) of the reticle 5 surface. With this arrangement, the disadvantageous effects of the diffraction lights from the circuit pattern can be minimized and substantially only the scattered lights, coming backwardly from the particle on the reticle, are received or detected by the photodetector.

Where the optical axis of the light-collecting system is so disposed as to pass through the point P, it is desirable that the piints P and P' define, with respect to the point O, a large angle δ, preferably in the range of $60° < δ < 180°$, in regard to the improvements of the rate of exact detection of a foreign particle, being discriminated from the circuit pattern.

With regard to the direct transmission component of the light beam I (FIG. 7) that has been directly transmitted through the reticle 5 substrate, a similar angle "δ" may preferably defined, with respect to the point O, by the point P and by the point at which the directly transmitted light intersects the sphere S surface.

Also, in the present embodiment, it is desirable in regard to the improvement in the rate of exact discrimination of the foreign particle that the optical components are disposed so as to define an angle, not greater than ±45 degrees, between the optical axis of the collecting system 6 and the optical axis of the projecting system 4.

Where the optical axis of the light-projecting system has an angle of approx. 60 degrees with respect to the reticle 5 surface, the optical axis of the light-collecting system may preferably have an angle in the range of 15–90 degrees with respect to the reticle 5 surface, such that the optical axis of the light-collecting system lies on the light entrance side of the normal to the reticle surface.

Figure 8:
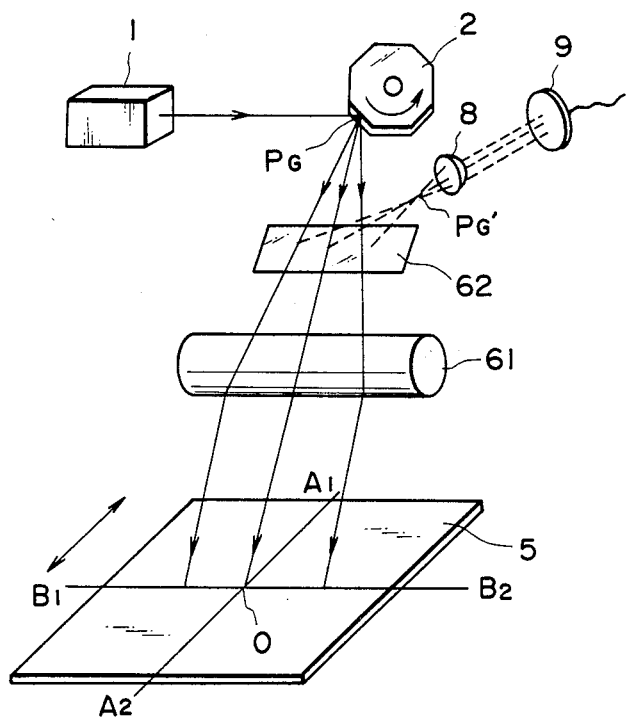
FIG. 8 is a schematic view showing a modified form of the embodiment of FIG. 6.

FIG. 8 is a schematic view showing a modified form of the examining apparatus of the FIG. 6 embodiment.

In this example, the light-projecting system and the light-collecting system 6 of the FIG. 6 embodiment are replaced by a single optical system 61, such that the scatteringly reflected rays from any foreign particle are collected in the same plane in which the scanning beam is projected upon the reticle 5. To achieve this, the mirror 7 of the FIG. 6 embodiment is replaced by a half mirror 62 which is adapted to transmit the scanning light beam from the polygonal mirror 2 and to reflect at least a portion of the light as collected by the projecting/collecting optical system 61. Description of the remaining portion of the present embodiment will be omitted here, by assigning like numerals to similar or corresponding elements.

In accordance with the present embodiment, as will be readily understood from FIG. 8, the optical arrangement of the apparatus can be made very simple and compact. In this embodiment, the optical system 61 as the light-projecting system has an optical function like an f-θ lens system, as in the foregoing embodiments and, such that the optical system 61 as the light-collecting system commonly uses such portion having the f-θ lens function.

In the optical arrangements shown in FIGS. 6 and 8, the lens system 8 may have an optical function or forming an image of the point $P_G'$ on the light-receiving surface of the photodetector 9. Alternatively, the optical components may be arranged so as to establish an optically conjugate relation between the reticle 5 surface and the light-receiving surface of the photodetector 9 such that the light beam from the point $P_G$ (which is a parallel beam) is directed to the photodetector 9.

In accordance with the present embodiment having been described with reference to FIGS. 6–8, a specific optical arrangement is employed so as not to receive diffracted lights from a circuit pattern of a reticle or photomask but, rather, so as to selectively receive or detect only the scattered lights (particularly, the scatteringly reflected lights) from any foreign particle on the reticle or photomask. Accordingly, the particle can be detected at a higher detection rate, while being discriminated from the circuit pattern.

Figure 9:
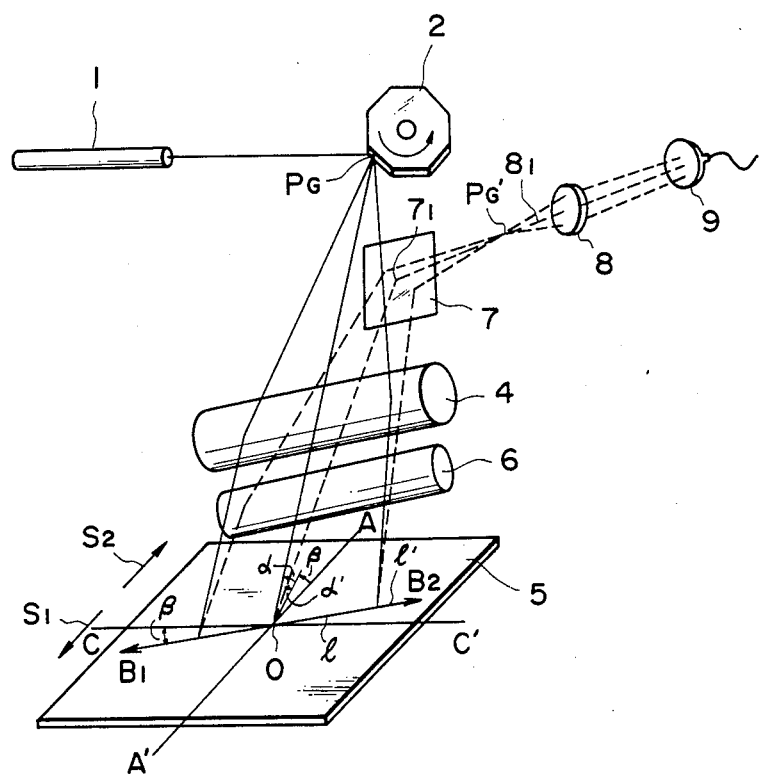
FIG. 9 is a schematic view showing an optical arrangement of a major portion of a surface examining apparatus according to a further embodiment of the present invention.
Figure 10:
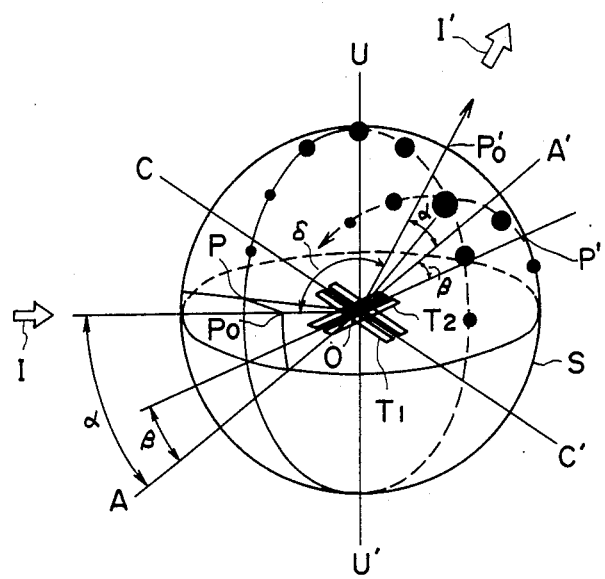
FIG. 10 is an explanatory view showing the relation between a light beam incident upon the surface being examined and the diffractively reflected light rays caused by a circuit pattern, in the case of the FIG. 9 embodiment.

Referring now to FIGS. 9 and 10, description will be made to a surface examining apparatus according to a further embodiment of the present invention. As will be understood from the following description, the surface examining apparatus of the present embodiment has advantageous features of both the FIG. 3 embodiment and the FIG. 6 embodiment, described hereinbefore, and exhibits a very good performance with regard to surface examination.

As shown, the examining apparatus includes a light source 1 such as a laser source for producing a laser beam, and a deflector 2 such as a polygonal mirror for scanningly deflecting the laser beam from the source 1. The laser beam deflected by the polygonal mirror 2 is incident on a light projecting optical system 4 which comprises a lens optical system including an f-θ lens and other elements. By this projecting system 4, the laser beam is perpendicularly incident upon the subject of examination, denoted at reference numeral 5, which in this example is a reticle used for the manufacture o semiconductor devices. A light-collecting optical system 6, comprising a lens optical system, is provided to collect light rays scattered (in this embodiment, scatteringly reflected) by dust or foreign particles deposited on the reticle 5. Mirror 7 is provided to reflect the scatteringly reflected light as collected by the collecting system 6, whereby the light from the collecting system 6 is directed to a lens system 8. Photodetector 9 is provided to receive the scatteringly reflected light as collected at or in the vicinity of a point $P_G'$ and passed through the lens system 8.

In the illustrated arrangement, the light beam from the laser 1 is reflected by the polygonal mirror 2 to the projecting system 4, by which it is converged, at a moment, upon one point (e.g. O) on the reticle 5 on which a circuit pattern is formed.

The polygonal mirror 2 and the projecting system 4 are cooperative with each other to provide a portion of light-projecting means. By rotating the polygonal mirror 2, the light beam from the laser 1 is scanningly deflected such that the surface of the reticle 5 is scanned in a direction from a point B1 to a point B2. Also, the reticle 5 is moved by suitable driving means, not shown, in a direction of an arrow S1 or S2. By this, substantially the whole surface of the reticle 5 is scanned with the light beam from the laser 1.

In the present embodiment, the light-projecting system 4 is disposed so that the light beam from the polygonal mirror 2 is projected upon the surface of the reticle 5 along a plane that is inclined relative to the reticle 5 surface and that intersects the reticle 5 surface along a line B1-B2 shown in FIG. 9. Also, the light-collecting system 6 is disposed so that its optical axis lies on the light entrance side of a normal of the reticle 5 surface. More specifically, the light-collecting system 6 is arranged such that its optical system lies between the reticle 5 surface and the plane along which the light beam from the polygonal mirror 2 is projected upon the reticle 5 surface by the projecting system 4. The collecting system 6 is adapted to collect a portion of the scattered lights (particularly, scatteringly reflected lights in this embodiment) from any foreign particle on the reticle 5 surface, at a position $P_G'$ or in the vicinity thereof, whereafter the light is directed to a light-receiving surface of the photodetector 9 by means of the lens system 8.

The collecting system 6, the mirror 7 and the lens system 8 are cooperative with each other to provide a portion of light-receiving means. The lens system 8 has an optical axis denoted at $8_1$ whose extension intersects the mirror 7 at a point $7_1$. The line connecting this intersection point $7_1$ and the point O on the reticle 5 corresponds to the optical axis $6_1$ of the collecting system 6. Also, the line connecting the point O and the reflection point $P_G$ on the polygonal mirror 2 corresponds to the optical axis of the projecting system 4.

It will be understood that the point $P_G'$ denotes the position at which or in the vicinity of which the light beam, having been emitted from the reflection point $P_G$ on the rotating polygonal mirror 2 and having been incident upon the reticle 5 by way of the projecting system 4 and further having been scatteringly reflected by a particle on the reticle 5, is collected by means of the collecting system 6.

In acordance with an important feature of the present invention, the collecting system 6 is also so arranged that the optical axis thereof, when projected upon the reticle 5 surface, extends in a direction different from the direction along which the diffraction light caused by a primary pattern on the reticle 5 advances or is projected. That is, the optical axis of the collecting system 6, when projected upon the reticle 5 surface, extends in the direction which is deviated from the direction of diffraction at the primary pattern on the reticle 5, by an angle β. The direction of the optical axis of the collecting system 6, when it is projectdd upon the reticle 5 surface, rotationally deviates from a line A—A' that is a reference direction corresponding to one of the primary diffraction directions, as in the FIG. 3 embodiment. Accordingly, the optical axis of the collecting system 6 has an azimuth "β".

In accordance with another important feature of the present invention, the scan of the reticle 5 surface with the light beam scanningly deflected by the rotating polygonal mirror 2 is made such that the line l connecting the points B1 and B2, i.e. the scan line l as determined by the one-dimensional scanning, extends in a direction different from the direction of diffraction caused by the primary pattern formed on the reticle 5. More preferably, the scan of the reticle 5 surface is made so that the scan line l rotationally deviates from the direction of diffraction at the primary pattern by an angle equal to the above-described angle β.

Where a plane which contains the optical axis of the collecting system 6 and the image of the same, as being projected upon the reticle 5 surface, is called a "meridional plane", a plane that is perpendicular to the meridional plane and that contains the optical axis of the collecting system 6 is a "sagittal plane". In the present embodiment, the optical components are so arranged that the line l defined on the reticle 5 surface by the scanning beam incident thereupon and the line l' along which the sagittal plane of the collecting system 6 intersects the reticle 5 surface, are substantially coincident with each other. Such arrangement is employed in order to collect the scatteringly reflected light rays efficiently so that a larger amount of light is directed to the photodetector 9.

It is to be noted however that the exact coincidence between the scan line l and the line l' of intersection of the sagittal plane of the collecting system 6 with the reticle 5 surface, is not always essential. These lines may deviate from each other within a range in which a sufficient amount of scatteringly reflected light from a foreign particle can be collected. It is also to be noted that the scan line l determined on the reticle 5 surface by the scanning beam from the projecting system 4 may be coincident with the direction of diffraction (diffracted light) caused by the primary pattern of the reticle 5, on the condition that the collecting system 6 is disposed with its optical axis, when projected upon the reticle 5 surface, extending in a direction different from the direction of diffraction caused by the primary pattern of the reticle 5.

FIG. 10 is an illustration showing a light beam projected upon the reticle surface, in the FIG. 9 embodiment, and diffractively reflected light caused by the circuit pattern of the reticle 5. In FIG. 10, the pattern bearing surface of the reticle 5 is depicted as being coincident with the equatorial plane of a sphere S which is schematically illustrated for explanation. Almost all the circuit patterns formed on photomasks or reticles, currently used in the manufacture of semiconductor devices, are provided by orthogonally extending pattern elements such as depicted at T1 and T2 in FIG. 10.

In FIG. 10, a light beam is projected upon the circuit pattern of the reticle 5 comprising pattern elements T1 and T2, in a direction of an arrow I so that it passes through a point Po on the surface of the sphere S. Namely, the light beam is projected at an incline from above with an angle of incidence "$\alpha$" and with an azimuth angle "$\beta$". Thus, the plane passing through points Po, O and P' is the plane of incidence along which the beam is projected. Accordingly, the light specularly reflected from the reticle surface advances in the direction of an arrow I' and intersects the sphere S surface at a point Po'.

If, on the other hand, the light beam is projected upon the reticle 5 surface in the direction from a point P on the sphere S surface to the point O, these points being contained in a plane parallel to the pattern elements T2, then the light specularly reflected from the reticle 5 surface advances to intersect the sphere S surface at a point P'. As has been described with reference to FIGS. 5A and 5B, there occurs an uninterrupted diffraction image (diffraction pattern) or, alternatively, discrete diffraction images (diffraction patterns) formed by diffraction lights of different diffraction orders and extending orthogonally to the pattern of the reticle. In the particular case of FIG. 10, wherein the circuit pattern comprises orthogonally extending pattern elements T1 and T2, there occur diffraction images (diffraction patterns) which are distributed substantially in two planes, as will be readily understood from the description having been made with reference to FIG. 7.

Further, as has been described with reference to FIG. 5C, when the examining beam is incident upon the primary pattern (T1 and T2) with an azimuth angle "$\beta$", such as denoted by arrows 51, the diffraction lights 52 and 53 from the primary pattern advance in the directions deviated from the direction of incidence of the light beam by the same angle "$\beta$".

In any case, the intensity or magnitude of the diffraction image (diffraction pattern) decreases with the increasing distance from the point Po' or P' at which the specularly reflected light from the reticle 5 surface intersects the sphere S surface. Particularly, in the plane denoted by Po-O-Po', the intensity of the diffraction pattern is not so high at a point of intersection at which the normal "u-O" intersects the sphere S surface, and it is very low at a point Po at which the incident light beam I intersects the sphere S surface.

As for the scattered light rays from a foreign particle, on the other hand, they advance isotropically or nondirectionally as described hereinbefore. Accordingly, even at the point Po or P or in the vicinity thereof, a significantly larger amount of light from the particle will be incident on the sphere S surface.

In the present embodiment, in view of this, the light-receiving means is so arranged that the optical axis of the light-collecting system 6 is disposed as far as possible from the path of the specularly reflected light I'.

More particularly, the light collecting system 6 is disposed such that its optical axis lies on the light entrance side (A-O-u) of the normal (u) of the reticle 5 surface and deviates from the directions of advancement of the diffracted lights from the primary pattern on the reticle. As a specific example, the optical axis of the collecting system 6 is positioned so as to pass in the vicinity of the point Po. With this arrangement, the disadvantageous effects of the diffraction lights from the circuit pattern can be minimized and substantially only the scattered lights, coming backwardly from the particle on the reticle, are received or detected by the photodetector.

More specifically, in the present embodiment, the light-collecting system 6 is so disposed that its optical axis has an angle "$\alpha'$" with respect to the reticle 5 surface, as best seen in FIG. 9, and also that the optical axis of the light-collecting system, when projected upon the reticle 5 surface, extends in a direction deviated by an angle "$\beta'$" from one of two orthogonal reference directions along which diffracted lights from the primary pattern of the reticle advance. In other words, the optical axis of the collecting system is positioned with the azimuth angle "$\beta'$". Further, in this embodiment, the light-projecting system 4 and the light-collecting system 6 are arranged so that their optical axes, when projected upon the reticle 5 surface, coincide with each other in order to assure that the scan line l defined on the reticle 5 surface by the scanning beam as projected by the light-projecting system 4 is exactly coincident with the line of intersection (l') along which the sagittal plane of the light-collecting system intersects the reticle 5 surface.

As described, the exact coincidence of the scan line l and the intersection line l', and, thus, the exact coincidence of the optical axes of the projecting system 4 and the collecting system 6, when projected upon the reticle 5 surface, are not essential and they may be deviative from each other, provided that a sufficient amount of scatteringly reflected light from any foreign particle can be collected by the collecting system 6.

According to the present embodiment, the light-projecting system 4 and the light-collecting system 6 are disposed in the specific positional relation described hereinbefore. By this arrangement, an improved detection rate for exactly detecting foreign particles, as being discriminated from the circuit pattern, is ensured. Also, as has been described with reference to the FIG. 6 embodiment, where the optical axis of thellight-collecting system 6 passes the point Po, it is desirable in regard to further improvement of the detection rate that the points Po and Po' define a large angle $\delta$ with respect to the point O, preferably in the range of $90° < \delta < 180°$.

Also, in the present embodiment, it is desirable in regard to the improvement in the rate of exact discrimination of the foreign particle that the optical components are disposed so as to define an angle, not greater than $\pm 45$ degrees, between the optical axis of the collecting system 6 and the optical axis of the projecting system 4.

In some case, as described hereinbefore, the circuit pattern of a reticle or photomask includes a pattern element which is inclined by an angle of 30, 45 or 60 degrees relative to the above-described reference directions (A—A' and C—C'). The inventors of the subject application have found that, in order to assure exact discrimination of any foreign particle adhered to a photomask or reticle having pattern elements extending in various directions, the light-collecting system 6 is so set that its optical axis, when projected upon the surface of the reticle, defines an angle of 15±5 degrees with respect to one of the two reference directions (A—A' and C—C') of the reticle (see FIG. 3). That is, the azimuth (β) of the optical axis of the light-collecting system is preferably in the range of 15±5 degrees.

In other words, the light-collecting system 6 is preferably disposed so that its optical axis, when projected upon the reticle 5 surface, has an angle in the range of 15±5 degrees with respect to one of the directions of two diffraction patterns, when projected upon the reticle 5 surface, caused by a circuit pattern comprising orthogonally extending pattern elements.

It is to be noted that the optical axis of the light-projecting system 4 and the optical axis of the light-collecting system 6 may be on the same side of a plane that contains the line C—C' and the normal to the reticle 5 surface, or alternatively they may be on the opposite sides of such plane. In any case, the advantageous effects of the present embodiment are attainable.

Figure 11:
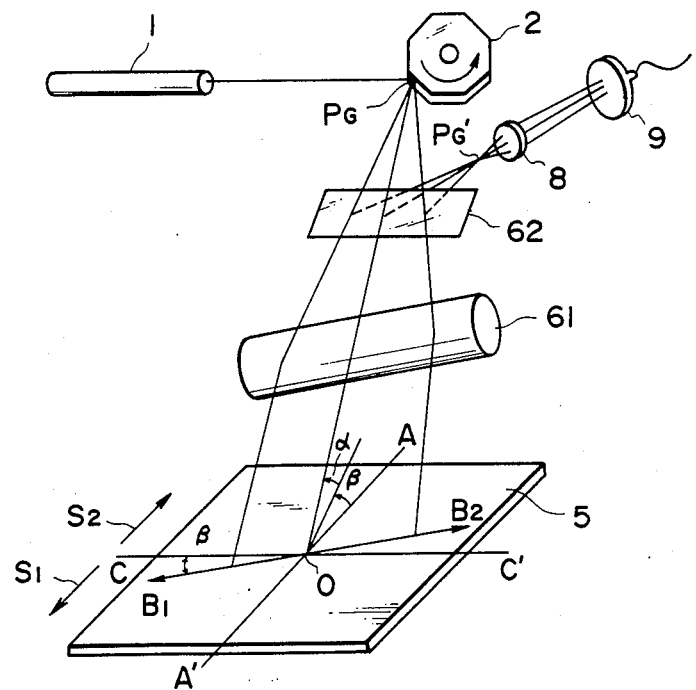
FIG. 11 is a schematic view showing a modified form of the FIG. 9 embodiment.

FIG. 11 is a schematic view showing a modified form of the FIG. 9 embodiment. In this example, similarly to the FIG. 8 example, the light-projecting system 4 and the light-collecting system 6 of the FIG. 9 embodiment are replaced by a single optical system 61, such that the scatteringly reflected rays from any foreign particle are collected in the same plane in which the scanning beam is projected upon the reticle 5. To achieve this, the mirror 7 of the FIG. 9 embodiment is replaced by a half mirror 62 which is adapted to transmit the scanning light beam from the polygonal mirror 2 and to reflect at least a portion of the light as collected by the projecting/collecting optical system 61. Description of the remaining portion of the present embodiment will be omitted here, by assigning like numerals to similar or corresponding elements.

In the optical arrangements shown in FIGS. 9 and 11, the lens system 8 may have an optical function for forming an image of the point $P_G'$ on the light-receiving surface of the photodetector 9. Alternatively, the optical components may be arranged so as to establish an optically conjugate relation between the reticle 5 surface and the light-receiving surface of the photodetector 9 such that the light beam from the point $P_G$ (which is a parallel beam) is directed to the photodetector 9.

In accordance with the present embodiments having been described with reference to FIGS. 9–11, a specific optical arrangement is employed so as not to receive diffracted lights from a circuit pattern of a reticle or photomask but, rather, so as to selectively receive or detect only the scattered lights (particularly, the scatteringly reflected lights) from any foreign particle on the reticle or photomask. Accordingly, the particle can be detected at a higher detection rate, while being discriminated from the circuit pattern.

In the embodiments as have been described hereinbefore, the light beam from the light source is scanningly deflected one-dimensionally while, on the other hand, the surface to be examined is moved in a direction different from the scan direction, thereby to examine the whole of the surface. As compared therewith, the whole-surface examination is also attainable by scanningly deflecting the light beam two-dimensionally. In such case, the light-collecting system is made movable so as to allow efficient collection of the scatteringly reflected rays from the surface. To the contrary, the surface itself may be moved two-dimensionally so as to achieve the whole surface examination. In such case, the light-projecting system, the light-collecting system and other optical components are fixed spatially.

In regard to the high-speed examination, it is desirable to scanningly deflect the light beam at least one-dimensionally. While, in the foregoing embodiments, the light-projecting system and the light-collecting system are fixedly secured and the subject of examination such as the reticle is moved in the direction different from the optical scanning direction, the subject of examination may be held immovable and, in place thereof, both the light-projecting system and the light-collecting system may be moved in the direction different from the optical scanning direction at the timing coordinated with the optical scanning.

While the invention has been described with reference to the embodiments wherein the examining apparatus is used to examine an object of rectangular shape, such as a reticle or photomask having a circuit pattern prepared for the manufacture of semiconductor devices, the invention is not limited to such case. For example, the surface examining apparatus of the present invention is suitably usable where the subject of examination, i.e. the surface or area to be examined, has a circular shape. In such case, the whole-surface examination is attainable by, for example, rotationally moving the object about the optical axis of the light-projecting system.

Further, the optical system constituting the light-collecting system may use either a single-lens optical system or a compound-eye lens optical system. Where the single-lens optical system is to be used, it may be provided by one or more ordinary spherical lens elements or toric lens elements such as cylindrical lenses. On the other hand, where the compound-eye lens optical system is to be used, it may be provided by a lens array comprising bar lenses, each having a curved lens surface at its input end and/or output end, or gradient-index type rod lenses each having an index distribution within the material thereof, these lenses are disposed in an array extending in a particular direction.

Further, the light-collecting system may comprise one or more bundles of light transmitting members such as optical fibers. In such case, the optical fibers may be used to directly receive the scattered light rays. Alternatively, the above-described lens array may be used to once collect the scattered light rays and to direct them toward the input ends of the optical fibers.

By establishing an imaging relation between the photodetector and the position of the surface, being examined, as irradiated by the light beam, and/or between the light-receiving surface of the light transmitting means for directing the scattered light to the photodetector and the position on the surface, being examined as irradiated by th light beam, accurate surface examination with increased efficiency of scattered-light collection is assured. This is because, if the above-described relation is established, any unwanted light scattered from a particle or particles adhered to a surface that is not being subjected to the examination, such as a non-pattern bearing surface of the retitle, can be effectively prevented from being detected by the photodetector.

In accordance with the present invention, as has hitherto been described, high-accuracy surface examination is ensured easily and stably. Moreover, such exact examination is, in principle attainable by use of a single photodetector, although two or more photodetectors may of course be used.

While the invention has been described with reference to the structures disclosed herein, it is not confined to the details set forth and this application is intended to cover such modifications or changes as many come within the purposes of the improvements or the scope of the following claims.

What is claimed is:

1. An apparatus for examining a surface of an object, the surface having a pattern formed thereon, and the object having a side extending in one direction, said apparatus comprising:

a light source;

an optical scanning system for scanning the surface of the object along a scan line with light from said light source;

a single photosensor; and a light guiding optical system, having an optical axis, for directing to said photosensor in uniform amounts a portion of light omnidirectionally scattered from each point on the surface of the object scanned along the scan line;

said light guiding optical system being disposed so that the optical axis thereof is inclined with respect to the surface of the object and is inclined with respect to the one direction in which the side of the object extends, such that a portion of the light omnidirectinally scattered from the surface of the object is directed by said light guiding optical system to said photosensor but light reflected from the surface of the object in a specific direction is not directed to said photosensor, whereby any foreign particle on each point on the surface of the object scanned along the scan line that omnidirectionally scatters light from the surface of the object can be discriminated by said photosensor.

2. An apparatus according to claim 1, wherein the optical axis of said light guiding optical system is inclined with respect to the one direction of the side of the object by an angle in a range of 15±5 degrees.

* * * * *

UNITED STATES PATENT AND TRADEMARK OFFICE
CERTIFICATE OF CORRECTION

PATENT NO. : 4,795,911

DATED : January 3, 1989

INVENTOR(S) : MICHIO KOHNO, ET AL.   Page 1 of 4

It is certified that error appears in the above-identified patent and that said Letters Patent is hereby corrected as shown below:

On the title page:

IN [30] FOREIGN APPLICATION PRIORITY DATA

"Japan .................... 61-30360
Japan ....................... 30361
Japan ....................... 30363"

should read

--Japan .................... 61-30360
Japan .................... 61-30361
Japan .................... 61-30363--.

COLUMN 1

Line 39, "Liid-Open" should read --Laid-Open--.

COLUMN 2

Line 10, "signfficantly" should read --significantly--.
Line 16, "sinnals" should read --signals--.

COLUMN 3

Line 21, "oonstituting" should read --constituting--.

UNITED STATES PATENT AND TRADEMARK OFFICE
CERTIFICATE OF CORRECTION

PATENT NO. : 4,795,911
DATED : January 3, 1989
INVENTOR(S) : MICHIO KOHNO, ET AL.

It is certified that error appears in the above-identified patent and that said Letters Patent is hereby corrected as shown below:

COLUMN 5

Line 25, "lasrr" should read --laser--.
    Line 59, "reticle" should read --reticle 5--.

COLUMN 6

Line 32, "pssition $P_G'$" should read --position $P_G'$--.

COLUMN 7

Line 14, "be" should be deleted.

COLUMN 8

Line 5, "eachoof" should read --each of--.

COLUMN 9

Line 64, "upo" should read --upon--.

COLUMN 10

Line 39, "poojecting" should read --projecting--.

COLUMN 11

Line 58, "piints" should read --points--.

UNITED STATES PATENT AND TRADEMARK OFFICE
CERTIFICATE OF CORRECTION

PATENT NO. : 4,795,911
DATED : January 3, 1989
INVENTOR(S) : MICHIO KOHNO, ET AL.    Page 3 of 4

It is certified that error appears in the above-identified patent and that said Letters Patent is hereby corrected as shown below:

COLUMN 12

Line 42, "or" should read --for--.

COLUMN 13

Line 11, "o" should read --of--.

COLUMN 14

Line 9, "acordance" should read --accordance--.
    Line 20, "projectdd" should read --projected--.

COLUMN 15

Line 21, "surface" should read --5 surface--.

COLUMN 16

Line 48, "thellight-collect-" should read --the
            light-collect- --.

UNITED STATES PATENT AND TRADEMARK OFFICE
CERTIFICATE OF CORRECTION

PATENT NO. : 4,795,911

DATED : January 3, 1989

INVENTOR(S) : MICHIO KOHNO, ET AL.    Page 4 of 4

It is certified that error appears in the above-identified patent and that said Letters Patent is hereby corrected as shown below:

COLUMN 18

Line 55, "th" should read --the--.
Line 61, "retille," should read --reticle,--.

Signed and Sealed this

Tenth Day of April, 1990

Attest:

HARRY F. MANBECK, JR.

Attesting Officer    Commissioner of Patents and Trademarks

UNITED STATES PATENT AND TRADEMARK OFFICE
CERTIFICATE OF CORRECTION

PATENT NO. : 4,795,911
DATED : January 3, 1989
INVENTOR(S) : MICHIO KOHNO ET AL.

It is certified that error appears in the above-identified patent and that said Letters Patent is hereby corrected as shown below:

COLUMN 4

Line 55, "views" should read --view--.

COLUMN 11

Line 66, "preferably" should read --preferably be--.

COLUMN 13

Line 25, "a" should read --one--.
Line 26, "one" should read --a--.

COLUMN 20

Line 8, "omnidirectinally" should read --omnidirectionally--.

Signed and Sealed this

Tenth Day of September, 1991

Attest:

HARRY F. MANBECK, JR.

Attesting Officer

Commissioner of Patents and Trademarks